United States Patent [19]

Möllering et al.

[11] 4,273,870

[45] Jun. 16, 1981

[54] METHOD AND COMPOSITION FOR THE DETERMINATION OF GLYCEROL

[75] Inventors: Hans Möllering, Tutzing; Siegfried Looser, Weilheim, both of Fed. Rep. of Germany

[73] Assignee: Boehringer Mannheim GmbH, Mannheim-Waldhof, Fed. Rep. of Germany

[21] Appl. No.: 54,728

[22] Filed: Jul. 5, 1979

[30] Foreign Application Priority Data

Jul. 18, 1978 [DE] Fed. Rep. of Germany ....... 2831580

[51] Int. Cl.³ .............................................. C12Q 1/32
[52] U.S. Cl. ..................................... 435/26; 435/190
[58] Field of Search ................... 435/4, 25, 26, 190; 424/2

[56] References Cited

U.S. PATENT DOCUMENTS

| | | | |
|---|---|---|---|
| 3,703,591 | 11/1972 | Bucolo et al. | 435/15 |
| 3,862,009 | 1/1975 | Wahlefeld et al. | 435/26 |
| 4,001,089 | 1/1977 | Stavropoulos et al. | 435/26 |
| 4,045,297 | 8/1977 | Weeks et al. | 435/26 |
| 4,142,938 | 3/1979 | Stavropoulos et al. | 435/26 |

OTHER PUBLICATIONS

Lin et al., "The Activation of Glycerol Dehydrogenase from *Aerobacter aerogenes* by Monovalent Cations, " *Journal of Biol. Chem.*, Jun. 1960, pp. 1820-1828.

*Primary Examiner*—Peter A. Hruskoci
*Attorney, Agent, or Firm*—Sprung, Felfe, Horn, Lynch & Kramer

[57] ABSTRACT

Method and composition for the determination of glycerol using glycerin dehydrogenase, an electron transfer agent, NAD and a tetrazolium salt and, in addition, at least one microgram of zinc, in the form of a zinc salt, per 50 U of glycerol dehydrogenase.

9 Claims, 1 Drawing Figure

TRIGLYCERIDE DYE TEST
GLYCEROL-DH/DIAPHORASE SYSTEM
TEST CONDITIONS:
- 0.1 MOLES/l. OF GLYCYL GLYCINE, pH 8.1
- 1.0 MILLIMOLES/l. OF SODIUM CHOLATE
- 0.1% GENAPOL X 080
- 0.12 MILLIMOLES/l. OF NITROBLUE TETRAZOLIUM CHLORIDE
- 1.5 MILLIMOLES/l. OF NAD
- $\geq$ 200 U/l. OF DIAPHORASE (CL. KLUYV.)
- $\geq$ 5000 U/l. OF GLYCEROL DEHYDROGENASE
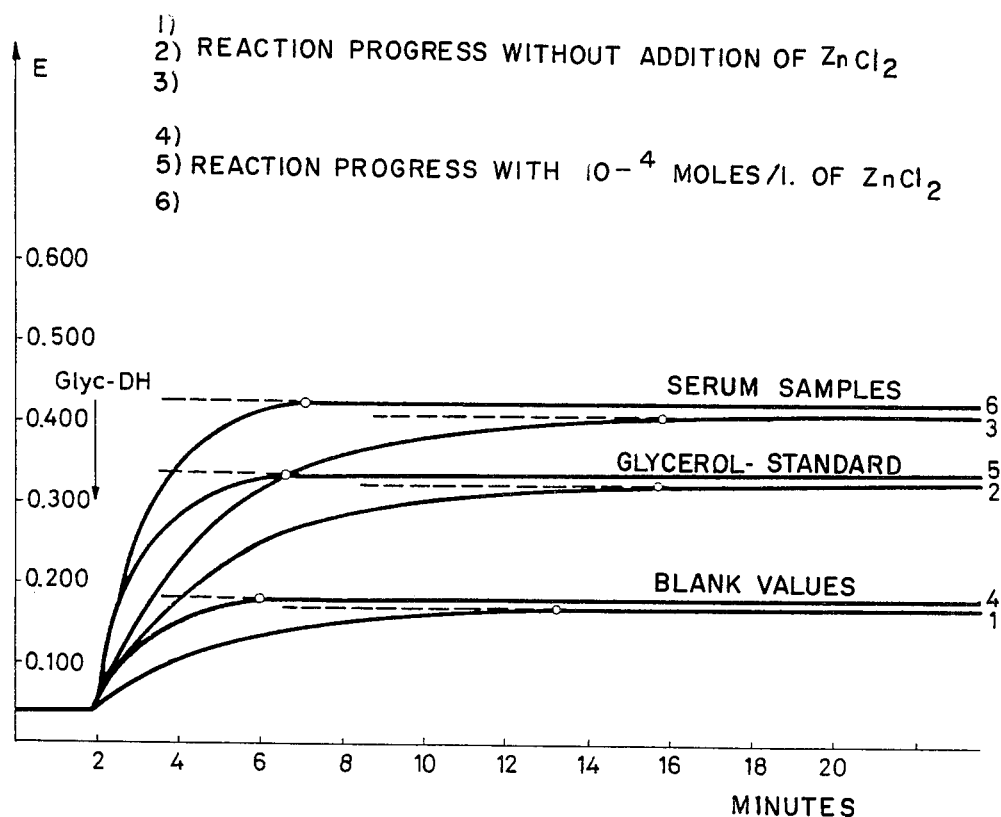

METHOD AND COMPOSITION FOR THE DETERMINATION OF GLYCEROL

The invention relates to a method and a reagent for the determination of glycerol.

A method is known for the determination of glycerol with glycerol dehydrogenase, diaphorase as electron transfer agent, nicotinamide-adenosine-dinucleotide (NAD) and tetrazolium salt, wherein a dye is formed which can easily be determined in visible or ultraviolet light depending on the tetrazolium salt that is used.

A disadvantage of this test is the slow start-up of the reaction. This is to be attributed to the glycerol dehydrogenase which takes a relatively long time to reach its maximum rate of reaction. It is furthermore found that, even if the same starting material is used for the production of the glycerol dehydrogenase, the latter is still subject to considerable variations in its rate of reaction. In the standardization of this test, therefore, a relatively long period of measurement must be prescribed for safety reasons, so as to assure that the maximum rate of reaction will be reached.

The invention substantially remedies this disadvantage and provides a method for the determination of glycerol which does not require the long measurement times required of prior art methods.

Essentially, the invention comprises a composition and method for determining glycerol using a glycerol dehydrogenase, an electron transfer agent, NAD and a tetrazolium salt and also comprising zinc, in the form of a zinc salt, in the amount of at least one microgram of zinc per 50 units of glycerol dehydrogenase.

The invention is based upon the surprising discovery that zinc ions in quite specific concentrations are capable of activating glycerol dehydrogenase to such an extent that its maximum speed of reaction is attained very rapidly. The maximum speed of reaction itself is not altered. The finding of the invention is surprising, since it was known through J. Biol. Chem. 235, No. 6, 1820 (1960) that zinc ions inhibit glycerol dehydrogenase. For example, a 50% inhibition has been described for a zinc concentration of $2.1 \times 10^{-5}$ M.

Zinc chloride is used preferentially as the zinc salt. However, other zinc salts having good solubility in water, whose anion has no harmful influence on the reaction, can equally be used. Typical examples of other suitable zinc salts are zinc sulfate, zinc acetate and the like.

The best results are obtained at a concentration between 0.01 and 1.0 millimoles per liter of zinc salt in the test mixture. If this maximum concentration is exceeded, the activation still takes place, but protein denaturation becomes increasingly perceptible and with it the occurrence of turbidity.

The method of the invention is suitable both for the determination of glycerol in biological fluids or other material and for use in connection with determinations of glycerol derivatives during which glycerol is liberated. The method is especially important for the determination of triglycerides, the saponification of triglycerides being performed preferably enzymatically, although it can also be performed alkalinely. Another example of a combined determination in connection with which the method of the invention can be used is the determination of phospholipids.

Other possibilities for the use of the method are the determination of glycerol ethers and glycerol esters, such as malic acid glycerol ester and citric acid glycerol ester, which are used as flavoring and perfumes; also, the determination of glycerol diesters and glycerol triesters which are also used as perfumes, in the form of acetin (glycerol triacetate) and butyrin (glycerol tributyrate).

The reaction of the invention is based on the following equations:

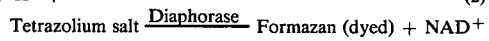

The preferred electron transfer agent is diaphorase. Examples of other electron transfer agents are phenazine methosulfate (PMS), 8-dimethylamino-2,3-benzophenoxazine (Meldola blue) and 1-methoxy-5-methylphenazinium-methylsulfate. Other electron transfer agents for tetrazolim salts are known to persons skilled in the art.

Numerous tetrazolium salts can be used within the scope of the method of the invention. These are known to the expert and need not further be described herein. Typical examples of suitable tetrazolium salts are nitro blue tetrazolium chloride (NBT), 3-(4',5'-dimethylthiazolyl-2)-2,4-diphenyltetrazolium bromide (MTT), 2-(p-iodophenyl)-3-(p-nitrophenyl)-5-phenyl tetrazolium chloride (INT), 2,2',5,5'-tetra-(p-nitrophenyl)-3,3'-(3-dimethoxy-4-diphenylene)-ditetrazolium chloride (TNBT), 2,3,6-triphenyltetrazolium chloride (TT) and neotetrazolium chloride (NT).

Additional subject matter of the invention is a reagent for determining glycerol, which is based on glycerol dehydrogenase, an electron transfer agent, NAD, tetrazolium salt and buffer, which is characterized by containing at least one microgram of zinc in the form of a zinc salt for every 50 units of glycerol dehydrogenase.

In a preferred embodiment, such a reagent contains:
5 to 20 U/ml of glycerol dehydrogenase,
0.2 to 1.5 U/ml of diaphorase,
0.5 to 5 millimoles/l of NAD,
0.1 to 0.5 millimoles/l of tetrazolium salt
0.05 to 0.2 moles/l of buffer, pH 7.5 to 9.0,
0 to 0.5% of detergent and
0.01 to 1.0 millimoles/l of zinc salt.

The above reagent can be in the form of a ready-to-use aqueous solution or in the form of a dry premix designed for dissolution in water or buffer solution, which then yields the above concentrations. In addition to the substances listed, the reagent can additionally contain stabilizers, such as ammonium sulfate, cholic acid and other such additives which are known to the expert. Glycyl glycine buffer is preferred as the buffer, 0.1 molar glycyl glycine buffer pH 8.0 to 8.2, being especially preferred. The diaphorase can be replaced by a corresponding amount of a different electron transfer agent.

If nitro blue tetrazolium chloride (NBT) is used as the tetrazolium salt, the measurement is best performed at 546 nm.

The reduction of the time required for glycerol determination which is achieved by the method of the invention can be seen in the appended FIG. 1 of the drawing, which shows the course of the reaction, represented as the extinction measured at 546 nm plotted against time. The curves 1, 2 and 3 show the progress of the reaction without the addition of zinc, the curves 4, 5 and 6 and progress of the reaction with the addition of $10^{-4}$ moles per liter of zinc chloride.

The test conditions were as follows:
0.1 moles/l of glycyl glycine buffer, pH 8.1,
1.0 millimoles/l of sodium cholate,
0.1% of detergent,
0.12 millimoles/l of NBT
1.5 millimoles/l NAD, 200 U/l of diaphorase,
5000 U/l of glycerol dehydrogenase.

After two minutes the reaction was started by the addition of the glycerol dehydrogenase. It can be seen that, in accordance with the invention, the maximum and constant reaction rate is reached within 4 to 5 minutes, while without the zinc additive steady values are not reached until after about 14 minutes. By the invention, therefore, the required reaction time is reduced to about one-third, which is equivalent to tripling the analysis capacity of automatic analyzers.

EXAMPLES

The following examples will serve to further explain the invention.

EXAMPLE 1

Combined Determination of Triglycerides by Cleaving and Measuring the Glycerol Released.

A reagent is used having the following composition:

| | |
|---|---|
| Glycyl glycine | 0.1 moles/l |
| pH | 8.1 |
| Ammonium sulfate | 100 mmoles/l |
| Cholic acid | 1.0 mmoles/l |
| Zinc chloride | 0.1 mmoles/l |
| Detergent | 0.1% |
| NAD | 1.5 mmoles/l |
| Tetrazolium salt | 0.12 mmoles/l |
| Lipase | 1.0 U/ml |
| Glycerol dehydrogenase | 15 U/ml |
| Diaphorase | 0.5 U/ml |

The determination is performed in the following manner:
Pipette into reagent glasses:

| | Blank value | Standard | Sample |
|---|---|---|---|
| Reagent solution | 2.0 ml | 2.0 ml | 2.0 ml |
| Standard | — | 0.02 ml | — |
| Serum | — | — | 0.02 ml |

Mix and incubate for 15 minutes at 20° to 25° C. Then, within the next 15 minutes measure the extinction of the sample and the extinction of the standard against the blank value. Incubation temperature: 20° to 25° C. Measuring wavelength: Hg 546 nm.

The computation of the result is performed according to the following formula:

$$c_{Pr} = \frac{\Delta E_{Pr}}{\Delta E_{St}} \times c_{St}$$

It will be understood that the specification and examples are illustrative, but not limitative of the present invention and that other embodiments within the spirit and scope of the invention will suggest themselves to those skilled in the art.

What is claimed is:

1. Method for the determination of glycerol, which method comprises contacting a sample with glycerol dehydrogenase, an electron transfer agent, NAD and a tetrazolium salt in amounts suitable for enzymatic activity and, in addition, at least one microgram of zinc, in the form of a water soluble zinc salt, per 50 units of glycerol dehydrogenase under conditions suitable for enzymatic activity; and determining the glycerol initially present in the sample by measuring the formation of dye.

2. Method as claimed in claim 1 wherein said zinc salt is $ZnCl_2$.

3. Reagent for the determination of glycerol comprising glycerol dehydrogenase, an electron transfer agent, NAD, tetrazolium salt, and buffer, in amounts suitable for enzymatic acitivity; and at least one microgram of zinc, in the form of a water soluble zinc salt, for every 50 units of glycerol dehydrogenase.

4. Reagent as claimed in claim 3 wherein said zinc salt is $ZnCl_2$.

5. Reagent as claimed in claim 3 wherein said zinc salt is zinc sulfate.

6. Reagent as claimed in claim 3 wherein said zinc salt is zinc acetate.

7. Reagent as claimed in claim 3 wherein said zinc salt is contained in an amount of from 0.01 to 1.0 millimoles of zinc salt per liter of reagent test mixture.

8. Reagent as claimed in claim 3 containing
   5 to 20 units/ml of glycerol dehydrogenase,
   0.2 to 1.5 units/ml of diaphorase,
   0.7+5 millimoles/l of NAD
   0.1 to 0.5 millimoles/l of tetrazolium salt, 0.05 to 0.2 moles/l of buffer, pH 7.5 to 9.5,
   0 to 0.5% detergent, and
   0.01 to 1.0 millimoles/l of zinc salt.

9. Reagent as claimed in claim 8 wherein said zinc salt is zinc chloride.

* * * * *

UNITED STATES PATENT AND TRADEMARK OFFICE
CERTIFICATE OF CORRECTION

PATENT NO. : 4,273,870
DATED : June 16, 1981
INVENTOR(S) : Hans Mollering et al.

It is certified that error appears in the above—identified patent and that said Letters Patent is hereby corrected as shown below:

On The Title Page, "OTHER PUBLICATIONS" citation, change "pp. 1820-1828" to -- pp. 1820-1823 --.

Claim 8, line 4, "0.7+5" to -- 0.5+5 --.

Signed and Sealed this

Sixth Day of July 1982

[SEAL]

Attest:

*Attesting Officer*

GERALD J. MOSSINGHOFF

*Commissioner of Patents and Trademarks*